United States Patent [19]

Colin et al.

[11] Patent Number: 4,995,540

[45] Date of Patent: Feb. 26, 1991

[54] UNIT DOSAGE DISPENSER FOR DENTAL IMPRESSION MATERIALS

[76] Inventors: Laurence Colin, Box 301, Cross River, N.Y. 10518; Edward R. Spehar, 49 Orion Way, Neshanic Station, N.J. 08853

[21] Appl. No.: 334,817

[22] Filed: Apr. 7, 1989

Related U.S. Application Data

[63] Continuation of Ser. No. 129,070, Dec. 7, 1987, abandoned, which is a continuation-in-part of Ser. No. 23,838, Mar. 9, 1987, Pat. No. 4,753,536.

[51] Int. Cl.⁵ .............................................. B67D 5/56
[52] U.S. Cl. ................................ 222/132; 222/137; 222/145; 222/459; 222/567; 433/90; 285/396
[58] Field of Search ............... 222/136, 137, 145, 276, 222/386, 459, 490, 567; 433/80, 89, 90; 285/396, 361

[56] References Cited

U.S. PATENT DOCUMENTS

| 322,286 | 7/1885 | Hemje | 285/361 |
|---|---|---|---|
| 617,591 | 1/1899 | Miller et al. | 285/361 |
| 1,193,446 | 8/1916 | Wells | 285/361 |
| 1,279,935 | 9/1918 | Sweat | 285/402 X |
| 1,549,858 | 8/1925 | Evans | 285/361 |
| 2,198,905 | 4/1940 | Cortert | 285/361 |
| 2,826,339 | 3/1958 | Maillard | 222/137 |
| 3,339,811 | 9/1967 | Haag | 285/361 |
| 3,386,626 | 6/1968 | Kearney | 222/567 X |
| 3,667,652 | 6/1972 | Morane et al. | 222/136 X |
| 3,739,947 | 6/1973 | Baumann et al. | 222/136 |
| 4,306,743 | 12/1981 | Hinshaw et al. | 285/402 X |
| 4,538,920 | 9/1985 | Drake | 222/137 X |
| 4,690,306 | 9/1987 | Staheli | 222/137 X |
| 4,747,517 | 5/1988 | Hart | 222/137 |
| 4,753,536 | 6/1988 | Spehar et al. | 222/494 X |
| 4,771,919 | 9/1988 | Ernst | 222/145 X |

FOREIGN PATENT DOCUMENTS 838157  6/1960  United Kingdom ............... 285/396

Primary Examiner—H. Grant Skaggs

[57] ABSTRACT

Apparatus for dispensing, in sequence, a unit dosage of several elastomeric impression materials of different viscosities so as to permit a dental impression to be taken under aseptic conditions in the preparation of a dental restoration. The apparatus also includes means for removably locking the syringe to the nozzle assembly.

1 Claim, 2 Drawing Sheets

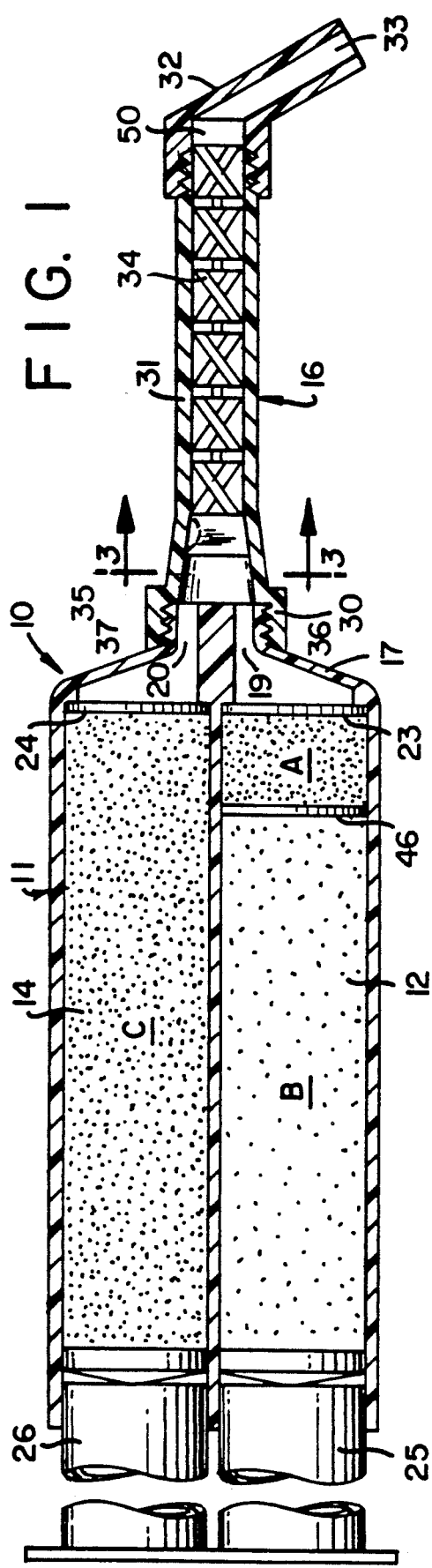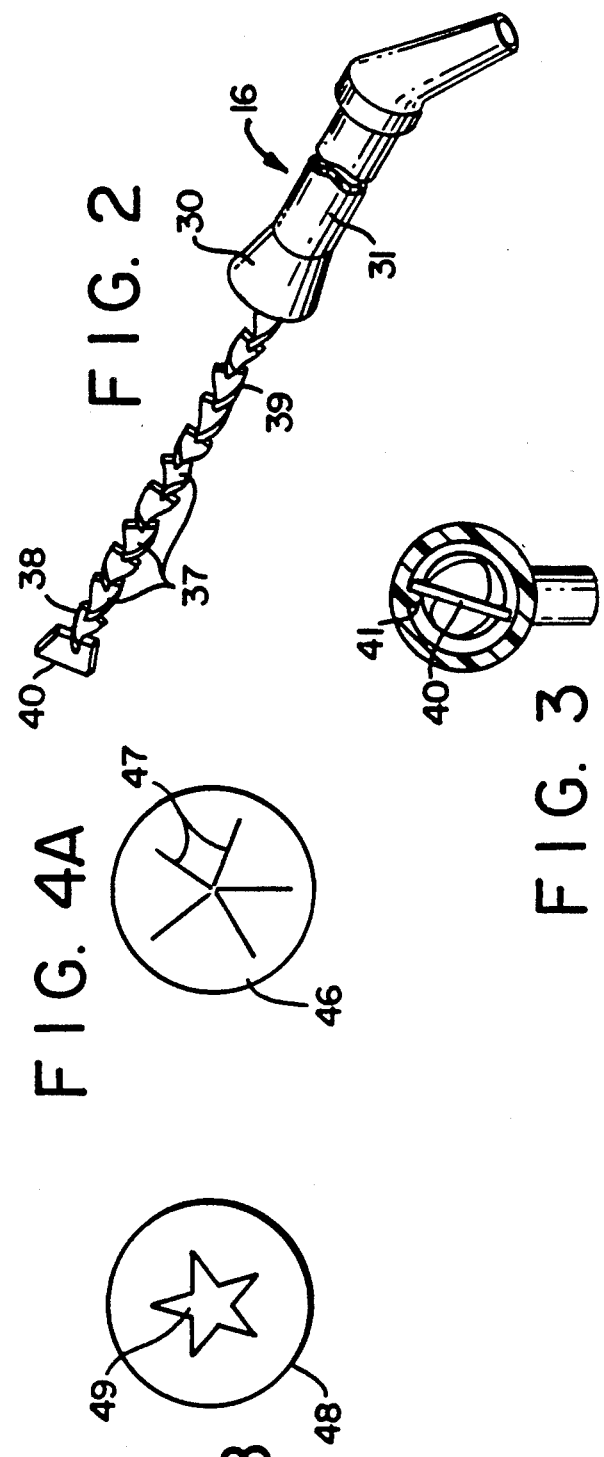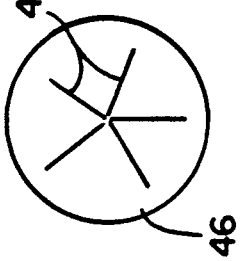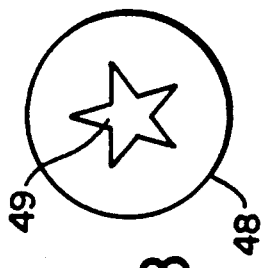

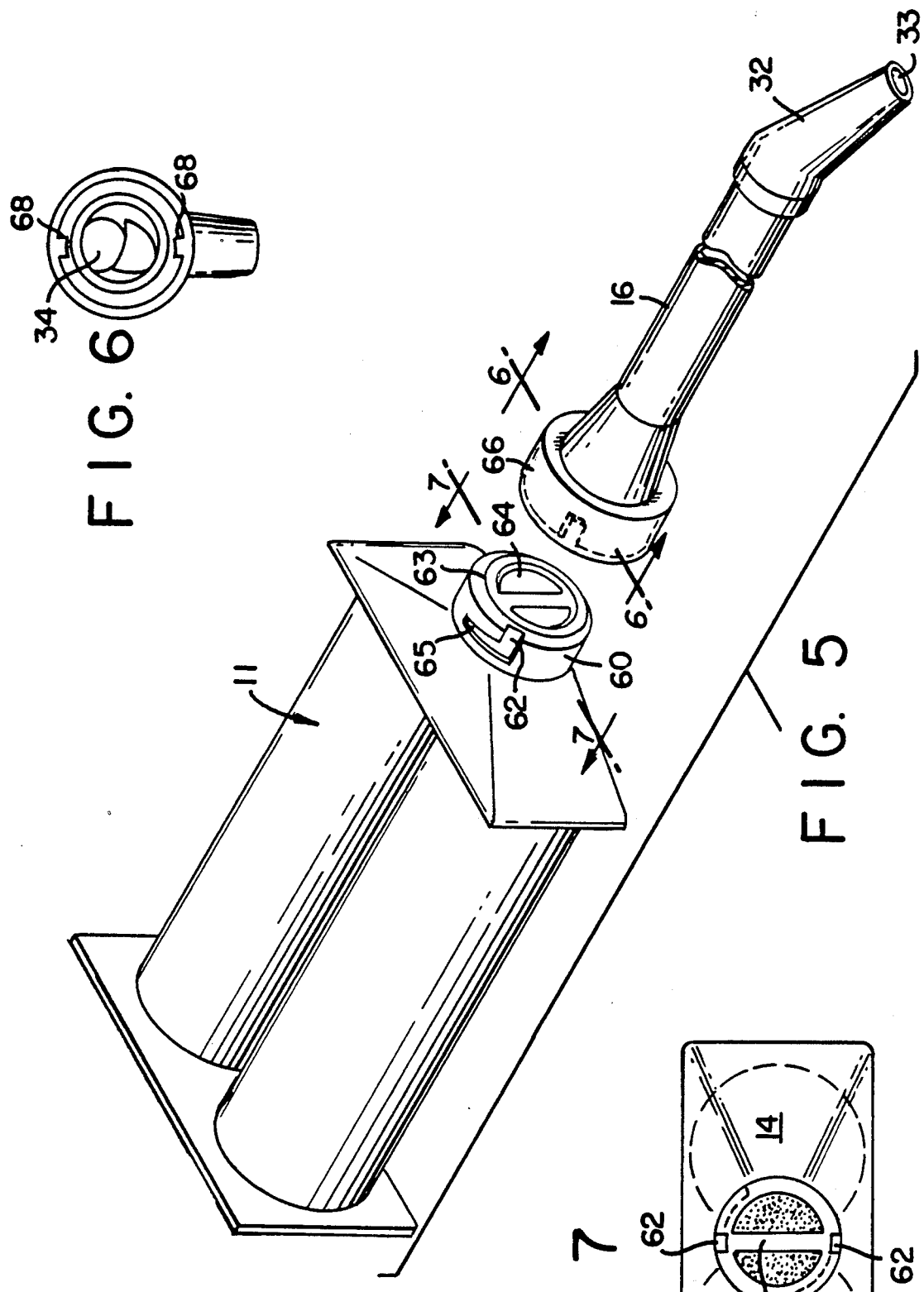

UNIT DOSAGE DISPENSER FOR DENTAL IMPRESSION MATERIALS

This application is a continuation of prior U.S. application Ser. No. 129,070; Filing Date Dec. 7, 1987 and/which is a continuation in part of application Ser. No. 023,838 Mar. 9, 1987 now U.S. Pat. No. 4,753,536.

FIELD OF INVENTION

More specifically this invention relates to apparatus for dispensing a unit dosage of different viscosity impression materials in sequence from a single source so as to permit a dental impression to be taken under aseptic conditions.

BACKGROUND OF THE INVENTION

Dental impressions of prepared and unprepared teeth are a vital step in the fabrication of the prosthetic replacement. Such devices as inlays, onlays, full crowns and bridges as well as removable prosthetic devices require replication with accuracy. By means of an impression or negative duplication of the intraoral site, a dental laboratory can convert this reverse likeness to a positive of the original condition. The materials used for taking the impression have improved and presently the use of elastomers is considered the most accurate, stable and easily handled of the impression materials.

A dental impression tray is usually selected for the particular area of the mouth where the impression is to be taken. To obtain an impression of the teeth and surrounding soft tissue, it is desirable to coat the intraoral site with a low viscosity impression material followed by a separate application of a higher viscosity material. The low viscosity material fills the internal critical surfaces of the oral cavity to provide maximum detail, whereas the higher viscosity material serves as a bulking agent between the low viscosity material and the tray. Additionally, the higher viscosity material serves to develop hydraulic pressure to force the lower viscosity impression material into tight apposition to the oral tissue and hard tooth structure.

A bond is formed between the two impression materials as long as too much time does not elapse between the covering of the teeth with the low viscosity material and the seating of the tray with the higher viscosity material. Otherwise, there will be an imperfect coalescence of the two materials. Moreover, if the higher viscosity material is allowed to begin to set before the tray is seated, it will distort the impression.

Presently, the elastomeric impression materials are blended and premixed by hand from separate containers of catalyst and base with the mixed higher viscosity material added to the tray and separately formed lower viscosity material drawn into a syringe. Not only is the blending of each of the impression materials subject to inconsistency from one operation to another, but the overall operation is both messy and time-consuming, and is, in general, performed in the full view of the patient without regard to asepsis.

The apparatus of the present invention dispenses a plurality of different viscosity elastomeric impression materials from a single source in a predetermined sequence and in a predetermined unit dosage for use in taking a dental impression. In using the apparatus of the present invention there is no mess and the procedure is inherently aseptic.

SUMMARY OF THE INVENTION

In accordance with the present invention, an apparatus has been developed for dispensing, in sequence, a unit dosage of several elastomeric impression materials of different viscosities so as to permit a dental impression to be taken under aseptic conditions in the preparation of a dental restoration. The apparatus in accordance with one embodiment comprises:

a syringe having at least two elongated storage compartments laterally spaced apart with each compartment having a discharge end;

means for simultaneously applying pressure upon the opposite end of each compartment for discharging material from the discharge end of each compartment in common;

a nozzle assembly having a single nozzle for dispensing the materials discharged from said syringe, a head for coupling said nozzle assembly to said syringe, and a static mixing element in said nozzle for intermixing the materials fed to said nozzle;

a first impression material of relative low viscosity located in a first one of said storage compartments;

a second impression material of a substantially higher viscosity relative to the viscosity of said first impression material disposed in tandem with said first impression material in said first storage compartment;

a curing composition for said first and second impression materials located in a second storage compartment; and means for separating said first and second impression materials for minimizing intermixing thereof during storage prior to use and during the sequential discharge of each material through said first storage compartment until one of said two impression materials is completely discharged from said storage compartment.

The apparatus in accordance with another embodiment comprises:

a syringe having a common head and two elongated storage compartments laterally spaced apart and extending from said head, with each compartment having a discharge and terminating in said common head;

means for simultaneously applying pressure upon the opposite end of each compartment for discharging material from the discharge end of each compartment in common; and a nozzle assembly having a single nozzle for dispensing the materials discharged from said syringe, a static mixing element in said nozzle for intermixing the materials fed to said nozzle, and mean for removably coupling said nozzle assembly to said syringe with said means comprising a cylindrical member having tong-like projections for engaging the head of said syringe, and wherein the head of said syringe includes symmetrically disposed recessed grooves in alignment with the longitudinal axis of said syringe, and a curved recess in a plane substantially transverse thereto into which said tong-like projections are removably placed.

BRIEF DESCRIPTION OF DRAWINGS

The arrangement and configuration which best illustrates the preferred embodiment of the invention is illustrated in the accompanying drawings which are to be considered as exemplary rather than limiting, and wherein:

FIG. 1 is a side elevation in cross section of the dispensing apparatus of the present invention;

FIG. 2 is an exploded view in perspective of the static mixing element and nozzle of FIG. 1;

FIG. 3 is a cross-sectional view of the nozzle assembly taken along the lines 3—3 of FIG. 1;

FIG. 4A is a plan view of one embodiment of the separating diaphragm for separating the impression materials in FIG. 1;

FIG. 4B is a plan view of another separating diaphragm for separating the impression materials in FIG. 1;

FIG. 5 is an exploded view of the dispenser of FIG. 1 employing an alternate arrangement for removably coupling the syringe and nozzle assembly;

FIG. 6 is a cross-sectional view of the dispenser of FIG. 5 taken along the lines 6-6; and FIG. 7 is another cross-sectional view of the dispenser of FIG. 5 taken along the lines 7-7 of FIG. 5.

DESCRIPTION OF PREFERRED EMBODIMENT

The apparatus of the present invention comprises a multi-barrel dispenser (10) which, as shown in FIG. 1, includes a syringe (11) having two compartments (12) and (14) for storing at least two elastomeric, self-curing, impression materials of different viscosities each having a base or a catalyst constituent (A) and (B), or conversely, (B) and (A), and a corresponding catalyst or base (C). The components from each compartment are fed in common into a common nozzle assembly (16) where they intermix before discharge. Each impression material is discharged in common with a catalyst and in sequence with each other.

The dispenser (10) is preferably constructed to conform to the dispensing mixer described in the parent U.S. Ser. No. 023,838 now U.S. Pat. No. 4,753,536 filed on Mar. 9, 1987, the disclosure of which is herein incorporated by reference. The syringe (11) is preferably molded from any plastic composition such as polystyrene with each of the compartments (12) and (14) being preferably of a cylindrical configuration and of equal size and volume. Each storage compartment (12) and (14) has a discharge opening (19) and (20) for expelling impression material through the head (17) of the syringe (11). A partition (18) which is molded in the body of the syringe (11) separates the discharge openings (19) and (20) until the materials discharge in common into the nozzle assembly (16). A pair of thin diaphragm membranes (23) and (24) may be used to initially close off each of the discharge openings (19) and (20). The membranes (23) and (24) are normally closed members which readily open in response to a predetermined minimum driving force applied to each compartment from a pair of plungers (25) and (26). A diaphragm member (46) as shown in FIG. 4A having closed score lines (47) may be used for the membrane (23) and (24), respectively.

The nozzle assembly (16) includes a head (30), a common nozzle (31), a removable spout (32) and a static mixing element (34). The head (30) has threads (35) for threadably engaging complementary threads (36) in the head (17) of the syringe (11). The nozzle (31) extends from the head (30) to the removable spout (32). The spout (32) is threadably coupled to the nozzle (31) for easy replacement. Although the spout (32) is shown in FIG. 1 with internal threads, it may be externally threaded and the nozzle (31) internally threaded. The spout (32) is preferably tapered to provide a small discharge opening (33), which may have any desired cross-sectional shape and may also be angled.

The static mixing element (34) consists of a multiple number of serially arranged blades (37) which have a bowtie-like configuration. Each blade is twisted so that its upstream and downstream edges (38) and (39) are at a substantial angle to each other with each adjacent blade twisted in an opposite direction with respect to its preceding blade. An arm or flag-like member (40) extends from the first blade (37) at the end adjacent the head (30) and is adapted to rotably engage a spline (41) projecting from the nozzle (31) upon the ingress of impression material into the nozzle (31), i.e., the impression material as it is discharged into the nozzle (31) causes the static mixing element (34) to rotate until the arm (40) hits the projecting spline (41). The initial placement of the static mixing element (34) within the nozzle (31) is arbitrary. It may simply be dropped into the nozzle (31) during assembly.

The storage compartments of the dispenser (10) are preloaded with elastomeric impression materials in a predetermined manner to form predetermined unit dosages, as hereafter explained. The compartment (12) is arbitrarily loaded with the base impression materials (A) and (B), or (B) and (A), respectively, with the base materials (A) and (B) separated by a diaphragm such as 46. Compartment (14) is loaded with a catalyst (C) for use in common with each of the base materials (A) and (B) or alternatively with a separate catalyst for each base impression material. The diaphragm (46) opens in response to a predetermined driving pressure for discharging material from each compartment in common.

The elastomeric impression materials are selected from any known self-curing materials, preferably a silicone elastomeric impression material consisting basically of a diorganopolysiloxane such as divinylpolysiloxane and an organosilicon cross-linker, preferably containing silicone bound hydroxyl groups. The catalyst is preferably platinum siloxane complexes.

The base impression material (A) is a low viscosity material for directly coating the intraoral site whereas impression material (B) is of a substantially higher viscosity material. The base impression material (B) is loaded into compartment (12) containing impression material (A) in a tandem arrangement separated by the diaphragm (46), having the configuration as shown in FIG. 4A or by a thin wafer-like diaphragm (48) as shown in FIG. 4B. The diaphragm (48) has an opening (49), preferably centrally located, to allow the more viscous impression material (B) to be discharged following the discharge of impression material (A). The diaphragm (46) separating the base impression materials (A) and (B) is primarily intended to prevent splashback of the low viscosity material (A) when the high viscosity material (B) is loaded into compartment (12). It also prevents any significant intermixing of the high and low viscosity materials when pressure is applied to drive the impression materials through the discharge openings (19) and (20).

The quantity of the base impression materials (A) and (B) are premeasured to provide predetermined unit dosages when mixed with catalyst (C).

The base impression materials and catalyst are driven from the compartments (12) and (14) by plungers (25) and (26) or by any other conventional drive mechanism. The plungers (25) and (26) are preferably coupled together to be driven in unison by, e.g., a conventional double-barreled, ratchet-type gun (not shown), which may be mechanically or automatically activated.

The dispenser (10) is operated to discharge the mixed impression materials (A) and (B) in sequence with the low viscosity material exruded intraorally directed upon the patient's teeth through the spout (32), followed by extrusion of the higher viscosity material directly in the dental tray. It is preferable to remove the spout (32) after the low viscosity material is fully extruded. Upon removal of the spout (32), the discharge opening (50) of the nozzle (31) provides an opening which is larger than the orifice (33) of the spout (32) permitting the more viscous impression material to be readily extruded into the dental tray. The impression materials may also be different colors to simplify the process for the dentist. In this fashion, the dentist can complete an impression under controlled aseptic conditions in an efficient manner.

The spout (32) may be replaced with a spout having a rectangular cross section to provide a flat ribbon of impression material for use intraorally. By placing impression material on the biting surface of the teeth, the patient, upon closing the upper and lower teeth, forms an intraocclusal record. This may be used by the dental laboratory to relate the opposing case models during fabrication of the prosthesis, so that proper contour and interdigitation can be accomplished.

The following compositions may be used for the high and low viscosity materials and for the catalyst:

EXAMPLE COMPOSITIONS

| Catalyst "C" | Viscosity Range |
|---|---|
| 10,000 cps of divinylpolysiloxane | 50,000–250,000 based on type of filler and percent filler loading |
| Platinum complex Inert silica fillers | |

BASE IMPRESSION MATERIALS

| Low Viscosity "A" | Viscosity Range |
|---|---|
| 4,000 cps of divinylpolysiloxane | 10,000–150,000 based on type of filler and percent filler loading |
| SiH cross-linking agent Inert silica fillers | |

Durometer when set is 45 Shore A

| High Viscosity "B" | Viscosity Range |
|---|---|
| 10,000 cps of divinylpolysiloxane | 200,000–600,000 based on type of filler and percent filler loading |
| SiH cross-linking agent Inert silica fillers | |

Durometer when set is 55 Shore A

In the dispensing apparatus (10) of FIG. 1, the syringe (11) is removably coupled to the nozzle assembly (16) using a threaded syringe and a complementary threaded nozzle. An alternative closure arrangement for removably coupling the syringe (11) to the nozzle assembly (16) is shown in FIGS. 5, 6 and 7. The syringe (11) has a cylindrical head (60) with a recessed groove (62) located symmetrically on opposite sides of the head (60). Each groove (62) is aligned parallel to the longitudinal axis of the syringe and extends from a chamfer (63) at the mouth (64) of the syringe (11) to a connecting recess (65) which circumscribes an arc lying in a plane, substantially transverse to the groove (62) or at a small acute angle relative thereto. The nozzle assembly (16) has a complementary cylindrical head (66) extending from the nozzle (31). The diameter of the head (66) is slightly larger than the diameter of the corresponding head (60). The head (66) has two tong-like projections (68) on opposite sides which are adapted to fit into the recessed grooves (62). To assemble the head of the nozzle into the syringe, the head (66) is positioned over the head (60) with the tongs (68) aligned with the recessed grooves (62). The tong-like projections are slid down into the grooves (62) until the tong-like projections (68) reach the curved recess (65), at which time the head (6) is rotationally twisted to lock the projections (68) into the curved recess (65). This provides a pressure lock which can withstand the forces generated when dispensing impression material.

What is claimed is:

1. Apparatus for dispensing a unit dosage of elastomeric impression material for taking an impression in the oral cavity under aseptic conditions in the preparation of a dental restoration comprising:

a syringe having at least two elongated storage compartments laterally spaced apart with each compartment having a discharge end;

means for simultaneously applying pressure upon the opposite end of each compartment for discharging material from the discharge end of each compartment in common;

a nozzle assembly having a single nozzle for dispensing the materials discharged from said syringe, a head for coupling said nozzle assembly to said syringe, and a static mixing element in said nozzle for intermixing the materials fed to said nozzle;

a first impression material of relative low viscosity located in a first one of said storage compartments;

a second impression material of a substantially higher viscosity relative to the viscosity of said first impression material disposed in tandem with said first impression material in said first storage compartment;

a curing composition for said first and second impression materials located in a second storage compartment; and means for separating said first and second impression materials for minimizing intermixing thereof during storage prior to use and during the sequential discharge of each material through said first storage compartment until one of said two impression materials is completely discharged from said storage compartment.

* * * * *